(12) United States Patent
Yanamoto

(10) Patent No.: US 9,968,585 B2
(45) Date of Patent: May 15, 2018

(54) PREVENTION OR TREATMENT AGENT FOR CEREBRAL AMYLOID BETA STORAGE DISEASES

(71) Applicant: TOYAMA CHEMICAL CO., LTD., Shinjuku-ku (JP)

(72) Inventor: Hiroji Yanamoto, Mino (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days. days.

(21) Appl. No.: 15/118,671

(22) PCT Filed: Feb. 16, 2015

(86) PCT No.: PCT/JP2015/054185
§ 371 (c)(1),
(2) Date: Aug. 12, 2016

(87) PCT Pub. No.: WO2015/122524
PCT Pub. Date: Aug. 20, 2015

(65) Prior Publication Data
US 2017/0049744 A1 Feb. 23, 2017

(30) Foreign Application Priority Data
Feb. 14, 2014 (JP) ................. 2014-042109

(51) Int. Cl.
*A61K 31/352* (2006.01)
(52) U.S. Cl.
CPC ................. *A61K 31/352* (2013.01)
(58) Field of Classification Search
CPC .................................. A61K 31/352
See application file for complete search history.

(56) References Cited

U.S. PATENT DOCUMENTS

2004/0138296 A1* 7/2004 Robertson ............ A61K 31/18
514/461

FOREIGN PATENT DOCUMENTS

| EP | 0 695 547 A1 | 2/1996 |
| JP | 11-193231 A | 7/1999 |
| JP | 3521145 B2 | 4/2004 |
| JP | 2005-539024 A | 12/2005 |
| WO | WO 2004014367 A2 * | 2/2004 ............ A61K 31/18 |

OTHER PUBLICATIONS

Hashimoto, M., et al. "Role of Protein Aggregation in Mitochondrial Dysfunction and Neurodegeneration in Alzheimer's and Parkinson's Diseases." NeuroMolecular Medicine. (2003), vol. 4, pp. 21-35.*
Davies, P., et al. "Mechanism-based treatments for Alzheimer's disease." Dialogues Clin. Neurosci. © 2009. pp. 159-169.*
Toshiharu Suzuki, "Aβ no Sansei o Seigyo suru Idenshigun no Hatsugen Chosetsu Kiko", Journal of Japanese Biochemical Society, Aug. 25, 2000, vol. 72, No. 8 (2 pages).
Seigo Tanaka, et al., "Alzheimer-byo Aβ Oyobi NAC Amyloid ni yoru NF-κB Kasseika Kiko", Journal of Japanese Biochemical Society, Aug. 25, 2001, vol. 73, No. 8 (2 pages).
Masaki Kikugawa, et al., "Enzymatic synthesis of hydrosoluble cinnamic acid esters and their improvement effect of Alzheimer's disease", Japan Society for Bioscience, Biotechnology, and Agrochemistry, Taikai Koen Yoshishu, Mar. 5, 2011 (2 pages).
Qi-Hai Gong, et al., "Resveratrol Attenuates Neuroinflammation-mediated Cognitive Deficits in Rats", Journal of Health Science, 2010, vol. 56, No. 6, pp. 655-663.
D. Jaturapatporn, et al., "Aspirin, steroidal and non-steroidal anti-inflammatory drugs for the treatment of Alzheimer's disease (Review)", The Cochrane Collaboration, 2012, Issue 2, (54 pages).
Hideya Sakaguchi, et al., "Cerebral Amyloid Angiopathy-related Inflammation Presenting with Steroid-responsive Higher Brain Dysfunction: Case Report and Review of the Literature", Journal of Neuroinflammation, 2011, vol. 8, No. 116, pp. 1-10.
Keiichi Tanaka, et al., Folia Pharmacol. Jpn., 2012, vol. 140, pp. 285-292.
Jiangtao Li, et al., "Efficacy and Safety of Iguratimod for the Treatment of Rheumatoid Arthritis", Hindawi Publishing Corporation. Clinical and Developmental Immunology, 2013, vol. 2013, Article ID 310628 (16 pages).
Justin Zaghi, et al., "Alzheimer disease macrophages shuttle amyloid-beta from neurons to vessels, contributing to amyloid angiopathy", Acta Neuropathol., 2009, vol. 117, pp. 111-124.
International Search Report dated Apr. 28, 2015 in PCT/JP2015/054185 filed Feb. 16, 2015.

* cited by examiner

*Primary Examiner* — Noble E Jarrell
*Assistant Examiner* — John S Kenyon
(74) *Attorney, Agent, or Firm* — Oblon, McClelland, Maier & Neustadt, L.L.P.

(57) ABSTRACT

Provided is a prevention or treatment agent for cerebral amyloid beta storage diseases, that contains a substance capable of suppressing the progression, alleviating the symptoms, and improving cerebral amyloid beta storage diseases. This prevention or treatment agent for cerebral amyloid beta storage diseases has as an effective component thereof a compound (e.g., Iguratimod) indicated by formula (1) or a salt thereof and, as a result, is capable of preventing or treating cerebral amyloid beta storage diseases such as Alzheimer-type dementia or cerebral amyloid angiopathy.

7 Claims, No Drawings

PREVENTION OR TREATMENT AGENT FOR CEREBRAL AMYLOID BETA STORAGE DISEASES

TECHNICAL FIELD

The present invention relates to a preventive or therapeutic agent comprising a substance having an ameliorating effect on symptoms caused by cerebral amyloid β storage diseases such as Alzheimer-type dementia (hereinafter, referred to as AZD) and cerebral amyloid angiopathy (hereinafter, referred to as CAA).

BACKGROUND ART

AZD is a disease in which amyloid β accumulates mainly around nerve cells and it causes nerve injuries and cerebral hypofunction mainly involving cerebral atrophy and dementia. Diffuse cerebral atrophy including that of the hippocampus and the cerebral cortex such as the frontal and parietal lobes is observed by imaging of the head in AZD. Agents that have been found to have efficacy in ameliorating dementia are already present. However, such agents cannot stop the progression of the condition. None of these agents have been successful in the long-term prevention or amelioration of cognitive decline and complete cure of the disease. Many clinical trials using anti-inflammatory steroids or non-steroidal anti-inflammatory drugs (hereinafter, referred to as NSAIDs) have been carried out based on the finding that inflammation in the brain is involved in the progression of AZD pathologies. Taking into consideration both the efficacy and side effect of respective drugs, however, the overall report that "the use of these drugs cannot be recommended for the treatment of Alzheimer's disease" has been made (Non Patent Document 1).

CAA is a disease in which amyloid β accumulates mainly in the cerebrovascular vessel and it causes brain injuries such as local circulatory dysfunction in the brain (white matter lesions), intracranial bleeding and multiple cerebral micro-bleeding (single, multiple, or bilateral), and epilepsy seizure. Characteristic accumulation of amyloid β on the cerebrovascular wall is observed in histopathological examinations for CAA. Besides, CAA is known to be associated with infiltration of various inflammatory cells such as small lymphocytes, macrophages, acidophiles, and multinucleated giant cells and a large number of micro-bleeding. Unfortunately, their causes are not known and, like AZD, no radical preventive or therapeutic agent (effective in suppressing the progression of pathologies, but not for symptomatic therapies) for CAA has been developed yet.

The progress in head MRI image has made T2-weighted imaging (T2-W1) in practical use and identification of asymptomatic or symptomatic cerebral micro-bleeding that could not be found has thereby become possible. CAA has become possible to be diagnosed by detection of deep white matter lesions and multiple micro-bleeding observed in MRI images, without conventional biopsies and pathological diagnoses of the brain tissue. However, no radical preventive or therapeutic agents for the disease has been developed and only surgical treatments for some intracranial bleeding and symptomatic therapies for epilepsy seizures have been practiced.

For CAA, efficacy of therapies using anti-inflammatory agents such as high dose steroid (glucocorticoid) therapies has been suggested as well as for AZD (Non Patent Document 2). However, administration of high doses of steroid is known to be associated with severe side effects such as susceptibility to infection due to the suppression of immunocompetence and accompanying infections with viruses, bacteria, and fungi; gastric ulcer formation and gastrointestinal bleeding; decreased bone density and increased proneness to bone fracture; impaired glucose tolerance and sudden hyperglycemia and dehydration; appearance of various psychiatric symptoms including depression; and adrenal insufficiency. Steroids have a wide suppressing effect on protective responses of the body to infections. In the case that a CAA-like vasculitis is associated with some infection, a long-term administration of a steroid might aggravate the condition. Since a slight side effect may become fatal in both the diseases AZD and CAA and these diseases may develop in elderly patients, some patients stop treatment halfway or reduce the dose of steroid, being subjected to the risk of exacerbation (rebound) of symptoms.

CAA, as well as AZD, is considered to involve the mechanism of autoimmunity. Efficacy of combination therapies of an immunosuppressive agent (such as cyclophosphamide) and a high dose of steroid, based on the idea, has been reported (Non Patent Document 2). However, this method has not become a common practice. It is not known whether the autoimmunity attacks normal cerebrovascular vessels or a damaged intravascular material to be removed or amyloid β, which acts as a tissue damaging factor.

Iguratimod (or T-614), chemical name: N-(3-formamido-4-oxo-6-phenoxy-4H-chromen-7-yl) methanesulfonamide (Formula (A)) is an agent classified in an immunomodulator and different from conventional antirheumatic drugs (Patent Document 1). Human use (a clinical trial) was started in about 2003. Iguratimod is characterized by suppressing effects, in particular, on the production of interleukin-1 and 6 (IL-1/6) and tumor necrosis factor (TNFα) from monocyte lineage cells (macrophages) in inflammation. No conventional NSAIDs (for example, indometacin) and disease modifying antirheumatic drugs (for example, salazosulfapyridine, SASP) have been found to have such effects. Such effects are considered to be unique effects of iguratimod, which has the "chromone structure" (Formula (B)) (Non Patent Document 3).

Formula (A)

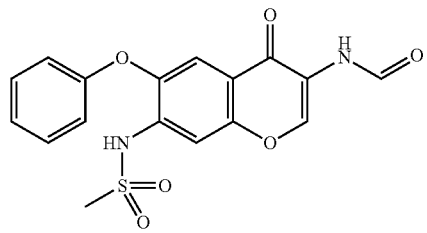

Formula (B)

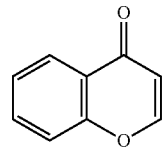

As therapeutic drugs for rheumatoid arthritis, efficacy of methotrexate (hereinafter, referred to as MTX), SASP, leflunomide, or cyclophosphamide, which are classified in immunosuppressive agents, has been already reported. And iguratimod has been also found to exhibit efficacy equivalent to MTX and SASP (Non Patent Document 4). Other therapeutic agents for rheumatoid arthritis include rituximab (trade name "Rituxan") effective against malignant lymphoma, the antibiotics minocycline and tetracycline, the hyperlipemic therapeutic drug statin, the multiple myeloma therapeutic drug thalidomide, and anti-JAK inhibitors, which inhibit JAK in signal transduction systems, suggesting the special nature of the disease rheumatoid arthritis.

Interleukin (IL) is the name of substances that are secreted from leukocytes and involved in the inflammatory reaction. Interleukins are numbered in the order of their identification. Over 30 ILs are now known. IL-1 and IL-6 are characteristic in that they are produced by locally activated monocytes (macrophages) and distinguished from cytokines that are produced by other cells classified as inflammatory cells such as T cells, B cells, NK cells, neutrophiles, mast cells, and peripheral blood monocytes.

PRIOR ART DOCUMENTS

Patent Document

Patent Document 1: JP 3521145 B

Non Patent Document

Non Patent Document 1: Cochrane Database of Systematic Reviews, Issue 2, Article ID: CD006378, 2012
Non Patent Document 2: Journal of Neuroinflammation, 8:116, 2011
Non Patent Document 3: Folia Pharmacol. Jpn., 140, 285-292, 2012
Non Patent Document 4: Hindawi Publishing Corporation Clinical and Developmental Immunology Volume 2013, Article ID 310628, 16 pages
Non Patent Document 5: Zaghi, J. et al., Alzheimer disease macrophages shuttle amyloid-beta from neurons to vessels, contributing to amyloid angiopathy, Acta Neuropathol., 2009, 117, 111-124.

SUMMARY OF INVENTION

Technical Problem

As to the conditions of AZD and CAA, it is known that amyloid β accumulates on nerve cells or the vascular wall. However, no radical preventive or therapeutic agent against the conditions has been developed yet. There have been demands for development of a novel preventive or therapeutic agent against these intractable conditions in which various symptoms are caused by the accumulation of amyloid β on nerve cells or the blood vessel in the brain, that suppresses the progression of the conditions safely, ameliorates mental and nervous symptoms, and maintains the ameliorated state or a tendency of the amelioration for a long time but not temporarily or transiently.

It has been reported that high dose steroid (or steroid pulse) therapies that widely suppress various inflammatory responses including humoral and cellular responses in the body were effective for AZD and CAA. However, this method remains under study and, because of severe side effects, it is not a kind of therapies that any physician can easily attempt.

Occurrence of injury in the body leads to inflammatory responses as a part of the body defense and also to secondary symptoms. Therefore, it is not clear whether the inflammatory responses suppressed by a steroid therapy having a wide anti-inflammatory spectrum are the cause or a result (secondary symptoms) of the conditions even if symptoms are at least temporarily suppressed by the steroid therapy. For example, cerebral edema, a local inflammatory body response to some brain injury (injury, stroke, brain tumor, metabolic disorder, etc.), can cause a new functional impairment in the brain by itself and will be treated by a steroid therapy having an anti-inflammatory action. However, as apparent from the fact that treatment of cerebral edema caused by infection with a medium to long-term steroid therapy may result in rather aggravation of the condition, steroid therapies, especially high dose steroid therapies, for edematous brain injury are only short-term and symptomatic measures.

Steroid (glucocorticoid) agents have diverse effects in the body. For example, steroids increase the production of lipocortin, IL-1 receptor antagonists, β2 receptors, IκB, and the like. On the other hand, steroids suppress the production of antibodies from B cells, arachidonate cascade, and the production of various cytokines, cell adhesion molecules, and the like.

In this regard, cytokines are soluble proteins that are produced by inflammatory cells and over 100 cytokines, including ILs, interferons (IFN), chemokines, growth factors, TNFs (tumor necrosis factors), and TGFs (transforming growth factors), are known. Even in the cases where a high dose steroid therapy has efficacy for AZD and CAA at least temporarily, the steroid should have effects on diverse points, such as effects on intracellular inflammatory cascade and effects on protein secretion and peptide production and on the production of other various inflammation-related substances, besides the regulation of expression of inflammation-related genes by the therapy. It is not known which cascade or substance among them is a target of an effective suppressing agent. Therefore, there have been demands for development of a novel preventive or therapeutic agent for AZD and CAA, which is specific to the cause of the diseases and safe.

Meanwhile, in Japan, an approval was given to the production of iguratimod as a drug with an indication for rheumatoid arthritis classified as a connective tissue disease in June, 2012. Iguratimod is, however, a therapeutic drug exclusively for rheumatoid arthritis in Japan. There has been no report that iguratimod was used for the purpose of ameliorating a condition (the state of disease) other than rheumatoid arthritis, for example, symptoms observed in CAA and AZD and the result indicated its efficacy.

An object of the present invention is to provide a substance that can suppress the progression of cerebral amyloid β storage diseases such as AZD and CAA, alleviate a symptom, and further ameliorate the disease.

Solution to Problem

The present inventor studied diligently to discover an agent that ameliorates conditions of cerebral amyloid β storage diseases in view of the aforementioned circumstances. As a result, the present inventor has found that administration of a compound having the chromone structure, such as iguratimod (N-(3-formylamino-4-oxo-6-phenoxy-4H-chromen-7-yl)methanesulfonamide), alleviates symptoms caused by cerebral amyloid β storage diseases such as AZD and CAA and exhibits efficacy stably and for a long time. No one has attempted the treatment of AZD and CAA with a compound having the chromone structure such as iguratimod so far.

The present invention achieves the aforementioned object based on the findings described above.

More specifically, the preventive or therapeutic agent for cerebral amyloid β storage diseases according to the present invention comprises, as an active ingredient, a compound represented by Formula (1):

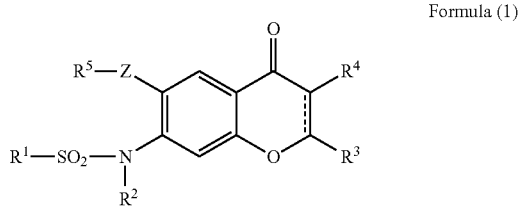

Formula (1)

In Formula (1), $R^1$ represents an alkyl, alkenyl or aryl group which may be substituted with a halogen atom;

$R^2$ represents a hydrogen atom, an alkyl group or an acyl group;

$R^3$ represents a hydrogen atom, a halogen atom, a cyano group, an azido group, a carboxyl group, a hydroxyl group, a formyl group or an alkoxycarbonyl group, or an optionally substituted alkyl, alkoxy, phenoxy, cycloalkyl, carbamoyl, amino or phenyl group;

$R^4$ represents a hydrogen atom, a halogen atom, a nitro group, a cyano group, a carboxyl group, an acyl group, a hydroxyl group or an alkoxycarbonyl group, or an optionally substituted alkyl, alkoxy, alkylthio, phenylthio, alkynyl, alkenyl, sulfamoyl, alkanesulfinyl, alkanesulfonyl, amidino, phenyl or heterocyclic group, or a group represented by Formula (2) or Formula (3);

$R^5$ represents an optionally substituted phenyl, thienyl, furyl or pyridyl group;

Z represents an oxygen atom, a sulfur atom or an imino group; and a dashed line represents a single bond or a double bond.

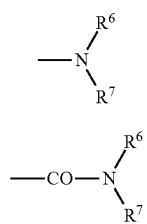

Formula (2)

Formula (3)

In Formula (2) and Formula (3), $R^6$ represents a hydrogen atom, a hydroxyl group, a cyano group or an alkoxycarbonyl group, or an optionally substituted alkyl, cycloalkyl, phenyl, amino, acyl, carbamoyl, alkanesulfonyl, iminomethyl or amidino group; and $R^7$ represents a hydrogen atom, an optionally substituted alkyl, alkoxy, phenyl, cycloalkyl or heterocyclic group, or $R^6$ and $R^7$ together with a nitrogen atom adjacent thereto represent an optionally substituted 3 to 7-membered heterocyclic group.

Advantageous Effects of Invention

According to the present invention, symptoms observed in cerebral 1-amyloid accumulation, for example, the diseases referred to as AZD or CAA, can be alleviated safely and the progression of condition can be prevented. More specifically, various cerebral (mental, nervous) functional impairment associated with AZD or CAA, which has not been possible to be cured, such as progression of dementia, listlessness, apraxia, agnosia, aphasia, incontinence, and gait disturbance can be ameliorated and quality of life can be improved.

DESCRIPTION OF EMBODIMENTS

The specific structure of a compound represented by Formula (1) (hereinafter, referred to as a compound of Formula (1)) is not particularly limited as long as it satisfies the requirements represented by Formula (1). The compound of Formula (1) is preferably a compound that satisfies one or more, preferably two or more, and further preferably three or more of the following limitations (A) to (D) and more preferably all of the limitations (A) to (D):

(A) The dashed line is preferably a double bond;

(B) $R^1$ is preferably a C1-C6 alkyl group, and more preferably a C1-C3 alkyl group;

(C) $R^5$ is preferably a phenyl group and Z is preferably an oxygen atom;

(D) $R^4$ is a group having preferably an acyl group (preferably a formyl group) as $R^6$.

The preventive or therapeutic agent for cerebral amyloid β storage diseases according to the present invention comprises, as an active ingredient, one or two or more of compounds represented by Formula (1) or salts thereof.

Specific examples of the compounds represented by Formula (1) include "iguratimod" (N-[3-(formylamino)-4-oxo-6-phenoxy-4H-chromen-7-yl]methanesulfonamide), which is represented by Formula (A) and known as an antirheumatic therapeutic agent under the registered trademarks such as Careram and Kolbet.

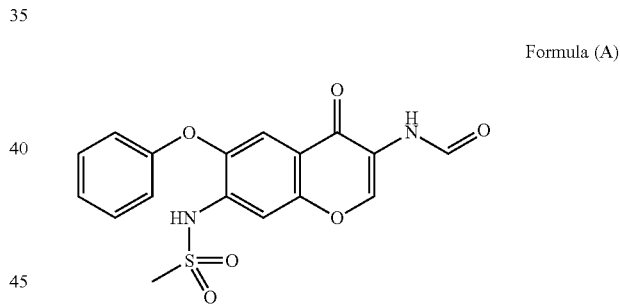

Formula (A)

The preventive or therapeutic agent of the present invention may comprise other components unless its preventive or therapeutic effect is inhibited. Specific examples of such other components include one or more other pharmaceutical components and one or more pharmaceutically acceptable additives. Examples of the aforementioned other pharmaceutical components include agents that suppress accumulation of cerebral amyloid β and agents that can alleviate symptoms observed in a disease caused by accumulation of intracerebral amyloid β, such as AZD or CAA, and prevent the progression of the condition. Specific examples of the aforementioned additives include excipients, disintegrators, diluents, emulsifiers, dispersants, adjuvants, preservatives, buffers, binders, stabilizers, coating agents, lubricants, flavoring agents, colorants, edulcorants, corrigents, suspending agents, and moistening agents.

The dosage form of the preventive or therapeutic agent of the present invention is not particularly limited unless its preventive or therapeutic effect is inhibited. The aforementioned dosage form may be any of a solid, a semisolid, and a solution. Specific examples of the aforementioned dosage form include tablets, coated tablets, pills, fine granules, granules, powders, capsules, syrups, emulsions, suspensions, injections, troches, and injections. The dosage form of the preventive or therapeutic agent of the present invention may be an extended or sustained release dosage form.

A compound of Formula (1) acts as an active ingredient in the preventive or therapeutic agent of the present invention. Thus, use of a compound of Formula (1) for production of a preventive or therapeutic agent for cerebral amyloid β storage diseases is disclosed herein. A compound of Formula (1) to be used for prevention or treatment of cerebral amyloid β storage diseases is also disclosed herein.

The aforementioned cerebral amyloid β storage diseases is not particularly limited to specific diseases as long as it is a disease caused by accumulation of amyloid β in cerebral tissue. Examples of the aforementioned cerebral tissue include nerves, glia, and blood vessels. In particular, examples of the aforementioned cerebral amyloid β storage diseases include mental or cranial nerve function impairments caused by accumulation of cerebral amyloid β. Specific examples of the aforementioned cerebral amyloid β storage diseases include AZD and CAA. Therefore, the preventive or therapeutic agent of the present invention can be particularly conveniently used as a preventive or therapeutic agent for AZD or CAA.

The preventive or therapeutic agent of the present invention can be used for prevention or treatment of cerebral amyloid β storage diseases, preferably AZD or CAA as described above. Therefore, a method for preventing or treating cerebral amyloid β storage diseases, preferably AZD or CAA by administering a compound of Formula (1) or a pharmaceutical composition comprising the compound to a patient with such a disease is disclosed herein. The mode of administration of the compound of Formula (1) or the pharmaceutical composition comprising the compound is not particularly limited unless its preventive or therapeutic effect is inhibited. The mode of administration may be oral administration or parenteral administration (for example, intravenous injection, intramuscular injection, drip infusion, nasal dropping, inhalation).

Examples of the symptoms caused by cerebral amyloid β storage diseases include various mental and cranial nerve functional impairment caused by accumulation of intracerebral amyloid β such as progression of dementia, central gait impairment, equilibration disorder, motor impairment, higher brain dysfunction, apraxia, agnosia, aphasia, incontinence, gait disturbance, anarthria, dysphagia and apathy and listlessness associated with AZD or CAA. The preventive or therapeutic agent of the present invention can alleviate symptoms observed in cerebral amyloid β storage diseases, for example, the diseases referred to as AZD or CAA and ameliorate mental and cranial nerve function impairments. The preventive or therapeutic agent of the present invention can suppress the progression of conditions caused by accumulation of intracerebral amyloid β. Thus, the preventive or therapeutic agent of the present invention can also be used for the prevention of cerebral amyloid β storage diseases.

The dose, regimen, combination with other agents, and administration period of the preventive or therapeutic agent of the present invention are not particularly limited. These can be selected depending on symptoms and the state of the patient as appropriate. The therapeutic agent of the present invention is preferably administered at a daily dose of 25 mg to 75 mg in terms of the active ingredient, a compound of Formula (1) (for example, iguratimod), in divided doses 1 to 3 times daily. The route of administration of the therapeutic agent of the present invention into the body is not also particularly limited.

The present inventor considers that the mechanism of action of the preventive or therapeutic agent of the present invention involves suppressing effect on the production of interleukins IL-1 and IL-6 and TNF-α. The present inventor considers that no known substance has the chromone structure and suppressing effect on the production of the aforementioned three substances. These are, however, simply the expression of the present inventor's view but not intended to define or limit the present invention.

The present invention will be described hereinafter with Examples on amelioration of symptoms caused by AZD and CAA by administration of iguratimod, but it is not intended that the present invention is limited thereto.

EXAMPLES

Example 1

Patient: 79 year-old male.

Family history: Father died of cerebral hemorrhage (type unknown) in his 50s. Older brother had CAA (cortical cerebral hemorrhage, symptomatic epilepsy) from his 60s, AZD from age 72, and died at age 76.

Past history: Since about 60 years old, deep white matter lesions (diagnosed by head MRI, T2-WI), lateral ventricular low density area (diagnosed by head CT), and moderate cerebral atrophy in the cerebral cortex including the hippocampus, parietal lobe, and frontal lobe and mild disturbance of memorization had been observed. However, there was no particular problem in everyday life.

History of present illness: At 76 years and 0 months old, walking difficulty (decreased speed and decreased stability of walking) appeared and then progressed slowly. Continuous walking of long distances of 600 m or more and walking with a heavy load (10 kg or more) in his hand or on his shoulder became difficult. Short-stepped gait and frontal gait appeared sometimes, with no fall. Cerebrovascular disorder was suspected and examinations by CT and MRI (other than T2-WI) were conducted. However, any responsible lesions, which were likely to develop relatively rapid walking difficulties, were not found, other than deep white matter lesions and moderate cerebral atrophy, which were observed previously. Parkinson's disease (syndrome) was also suspected and a therapeutic agent for the disease was temporarily administered, which was stopped because of the lack of efficacy. Furthermore, from about 77 years old, cognitive (memorization, storage, or recollection or all of them) ability declined, resulting in difficulties in selecting the correct route and in operating machinery, and driving of automobile was stopped (although the result of cognitive function and intelligence test was in the normal range). Instability of walking also progressed relatively rapidly and it became difficult to walk outdoor without a walking stick.

From 78 years and 0 months old, walking difficulties and cognitive impairment further progressed. A close examination at 78 years and 6 months old denied conditions, other than ALZ, which may cause dementia, including the following conditions: normal pressure hydrocephalus, folic acid or vitamin deficiency, depression, Parkinson's syndrome, cerebrovascular stenosis (chronic cerebral ischemia), neurological degenerative diseases, hypothyroidism, and vascular dementia. Meanwhile, MRI (T1/2WI, T2-WI) detected multiple micro-bleeding mainly in the area from bilateral basal ganglia (thalamus and hypothalamus) to upper brain stem and the patient was diagnosed with CAA. The patient was also diagnosed with AZD based on diffuse cerebral atrophy including hippocampus and a wide range of cerebral cortex and moderate dementia. From 78 years and 8 months old, Predonine (5 mg) for CAA and an NMDA inhibitor and an AZD therapeutic agent (memantine) for AZD were administered. However, no significant amelioration of walking impairment or cognitive impairment was observed, and both symptoms continued to progress.

From 78 years and 10 months old, further decline in energy and spontaneity, decrease of speech, and difficulty in writing own name were observed and the patient became barely capable of recalling people's name, suggesting overall decline in cerebral functions. For walking, an assistance, or at least handrail, became always necessary and continuous walking of distances of 50 m or more became difficult (unstable) even with an assistance. Furthermore, the patient was frequently found in a somnolence state even in the daytime and occasional decrease in the level of consciousness during meal caused difficulty in swallowing. At 78 years and 11 months old, standing and walking became impossible during a period of repeated high fever. Chest CT detected a sign of aspiration pneumonia and the patient was admitted to a nearby hospital.

Immediately after the hospitalization, administration of antibiotics against the pulmonary inflammatory disease was started and high dose administration of mineralocorticoid (200 mg injection of Hydrocortone/day, for 7 days in plan) was also started for the purpose of steroid supplementation against the potential hypoadrenalism (mineral imbalance), due to the previous sustained steroid (5 mg) therapy. From 3 days after the start of the steroid replacement therapy, increase in energy and speech, amelioration of cognitive function, and improvement of walking ability were observed, suggesting efficacy of the high dose steroid therapy for neurological symptoms (AZD and CAA). However, from Day 5 to 6 after the start of the mineralocorticoid administration, the symptoms gradually aggravated (the previous recovery disappeared), resulted in inability to walk, as well as disappearance of speech, increased somnolence (decreased level of consciousness), appearance of urine and fecal incontinence, and inability to have meal by oneself. On Day 9 after the hospitalization, the patient became almost bedridden and nonresponsive. On Day 10 after the hospitalization, administration of a high dose of glucocorticoid (30 mg/day of Predonine) for anti-inflammatory effect was therefore started for the purpose of ameliorating the cerebral hypofunction, based on the informed consent.

Starting the administration of a high dose of glucocorticoid (steroid) agent alleviated a neurological symptom (decrease in somnolence), increased energy and speech, and recovered abilities to tell desires to urinate or defecate, to walk with an assistance, and to have meal by oneself (with a spoon). However, from Day 20 after the hospitalization, a somnolence tendency appeared again and the symptoms of decline of cognitive ability, inability to walk, lack of speech, urine incontinence, apraxia and agnosia appeared again. Thus, it was revealed that a sustained glucocorticoid therapy at the maximum dose for the patient's age cannot prevent the progression of the symptoms (such as decline in cognitive ability, walking difficulties, decrease of energy and spontaneity, aphasia, apraxia, and agnosia) for 10 days or more (20 days or more from the start of high dose steroid administration).

Since no tendency to alleviate the symptoms was observed, on Day 22 after the hospitalization, administration of 25 mg of iguratimod (for example, the trade name "Kolbet" produced and sold as an antirheumatic drug by Taisho Toyama Pharmaceutical Co., Ltd. or the trade name "Careram" produced and sold by Eisai Co., Ltd.), in addition to the high dose glucocorticoid therapy, was started for the purpose of ameliorating cognitive impairment, walking impairment, decrease of energy and spontaneity, and aphasia, apraxia, and agnosia, based on the informed consent. Iguratimod is a novel therapeutic agent for rheumatoid arthritis having a suppressing effect on the production of cytokines from macrophages and its efficacy for cerebral amyloid β storage diseases (conditions associated with intracerebral amyloid β accumulation and symptoms thereof) has been unknown.

From Day 24 after the hospitalization (2 days after starting the administration of iguratimod), apparent amelioration of spontaneity was observed and amelioration of neurological symptoms (walking impairment associated with CAA and cognitive impairment associated with AZD) was also observed. Therefore, from Day 28 after the hospitalization, the dose of the steroid agent was reduced to 20 mg per day and, from Day 34 after the hospitalization, the dose of iguratimod was increased to 50 mg per day. The dose of the steroid agent was subsequently decreased gradually and it was reduced to 5 mg/day, the dose before the hospitalization, by Day 48 after the hospitalization.

After starting the administration of iguratimod, neurological symptoms related to walking and spontaneity (ability to speak, to have meal by oneself using a spoon, and to express desire to urinate and other wishes) were ameliorated and sustained. The patient was discharged 2 months after starting the administration (79 years and 2 months old), as amelioration of the following symptoms observed before the hospitalization: difficulty in swallowing and walking impairment, aphasia, agnosia, apraxia, agraphia, incontinence, lack of emotional expression, apathy, somnolence tendency, and cognitive impairment were observed. At the time of the discharge, continuous walking of about 50 m with an assistance was possible and the patient managed to walk up 8 steps of stairs with an assistance at both arms.

Cognitive ability, energy, spontaneity and speech, apraxia, and agnosia were further ameliorated also after the discharge. At 6 months after starting the administration (79 years and 6 months old), continuous walking of about 100 m with an assistance was possible and the patient managed to walk up 15 steps of stairs with an assistance and use of handrail. An examination by head MRI in the same period did not detect any appearance of novel vascular abnormality or progression of cerebral atrophy, in comparison with the MRI before starting the administration (78 years and 7 months old).

At one year after starting the administration of iguratimod (80 years and 0 months old), administration of the steroid agent, which is a wide spectrum anti-inflammatory agent, was stopped completely, which resulted in no aggravation of symptoms. From the same period, the patient regained interest in TV, making comments occasionally, and restarted watching sumo programs. The patient also regained ability to write the own name correctly, to recall names of places and people to some extent, and to recall pleasant experiences 1 week ago or earlier. Furthermore, the patient started responding to the sight of an infant with smiling, talking, and fondling.

As to eating behaviors, while the patient sometimes failed to bring food to the mouth at the time of discharge (3 months after starting the administration), At a half year after starting the administration, the patient was able to have meals by oneself using chopsticks (without spoiling his clothes or the surroundings). The patient had an increased walking difficulty and cognitive impairment at the time of the hospitalization. After the discharge, the frequency of incontinence decreased gradually and urination and defecation in toilet was possible during the day and night at several months after the discharge, which made possible to go to a public bath and to go on a hot springs trip with an attendant.

By one year after starting the administration of the agent, the patient became further capable of performing, in some degree, some programs using apparatuses for simple muscular exercise in a day-service rehabilitation facility and greetings to and thanking some of the facility staffs he recognized though he still needed a walking assistance to the place (apparatus). In the mini-mental state examination (MMSE), which is an assessment system for the cognitive function, the patient's score was 10 or less (severe dementia) before starting the administration of iguratimod, but it increased to 10 or more (moderate dementia) by one year after having started the oral administration.

In a head imaging examination by 3T-MRI:SWI at 7 months (79 years and 7 months old) and 19 months (80 years and 7 months old) after the beginning of iguratimod, the progression of cerebral atrophy and other lesions was not apparent. Increase or enlargement of polynesic multiple micro-bleeding in bilateral thalami, basal ganglia, brainstem, cerebellum, deep white matter, cerebrum gray matter, and the like (deposition of amyloid $\beta$ on the vascular wall and vascular abnormalities attributed to the infiltration of blood components into the vascular wall), which were observed previously, was not found by the imaging. Meanwhile, during the amelioration of the symptoms, no conventional dementia drugs other than iguratimod were administered. Therefore, suppression of the progression of, or ameliorating effect on: progressive cerebral atrophy and cognitive impairment caused by Alzheimer-type dementia (AZD); increase or enlargement of intracerebral micro-bleeding, progressive walking difficulty, and progressive difficulties of other daily living activities considered to be caused by cerebral amyloid angiopathy (CAA); and the like, is considered to be caused by the administration of iguratimod since no other reason therefor was found.

Discussion: As apparent from the fact that clinical symptoms and the MMSE score on the cognitive function and daily living activities were ameliorated and progression of cerebral atrophy and vascular abnormal regions (the number confirmed in the imaging and the area of individual microsignals) observed in cerebral imaging was suppressed after starting the administration of iguratimod, the progress of the conditions caused by cerebral amyloid accumulation was suppressed and the symptoms associated therewith were ameliorated.

However, no cerebral histological data (indicating that amyloid $\beta$ itself was decreased) indicating that the administration of iguratimod actually suppressed "the accumulation of intracerebral amyloid $\beta$" has been obtained. Accordingly, the present invention generally relates to amelioration of conditions and symptoms and preventive effect and more particularly to suppression of the progression of AZD and CAA caused by accumulation of intracerebral amyloid $\beta$ and cerebral atrophy and intracerebral micro-bleeding conditions associated therewith, amelioration (treatment) of symptoms associated therewith, and long-term (from a half year to one year or more) suppression of the progression of conditions (disease state and symptoms). For example, it is not necessary that the administration of the agent has an effect on the accumulation of intracerebral amyloid $\beta$ itself, but the agent may control (suppress or modulate) a subsequent intracellular or extracellular molecular cascade, thereby suppress the progression of cerebral atrophy and vascular abnormalities and ameliorate the symptoms. Either way, iguratimod and substances having a similar molecular structure and in vivo functionality can be used to prevent the progression of conditions caused by accumulation of intracerebral amyloid $\beta$ and ameliorate symptoms caused by the accumulation.

It has been revealed, based on the clinical course after the administration of iguratimod in the patient with complication of AZD and CAA in Example 1, that it suppresses at least the progression of conditions and ameliorates symptoms of diseases (for example, AZD and CAA) characterized by "progressive cognitive impairment" and "progressive decline of other cerebral functions" caused by accumulation of intracerebral amyloid $\beta$.

Example 2

An 81 years old female became indifferent to social activities and meeting people 3 to 4 years ago. Cognitive impairment appeared to the degree to cause difficulty in daily life activities 2 years ago. One year ago, cognitive impairment further progressed and MMSE was conducted to get scores of 14 or less. Since a head imaging detected moderate atrophy in the cerebral cortex including the parietal lobe and the hippocampus, the patient was diagnosed with "moderate dementia caused by AZD" based on the clinical and brain imaging observations. In the everyday life, disturbance of memorization was observed, in which the patient forgot contents of conversation in 5 minutes and purchased the same thing repeatedly when she went out alone. The patient liked cooking previously, but became unable to cook or adjust the taste. Spatial cognitive impairment was observed in which the patient got lost in the neighborhood and failed to go home, which made her difficult to go out alone. The patient became unable to manage own medication such as an antihypertensive agent (cognitive impairment on table and calculation) and management by a family member became necessary. Since efficacy (suppression of progressive symptoms) of a conventional drug against AZD was not observed for a half year or more, the administration of iguratimod at 25 mg/day was started, based on the informed consent to the patient and her family, and the dose was increased to 50 mg/day 4 weeks later.

At 3 months after starting the administration, the patient was able to go out (and go home) alone and symptoms such as getting lost and failing to go home and purchasing the same thing repeatedly had disappeared, although some symptoms such as forgetting what happened shortly before remained. Furthermore, the patient was able to purchase necessary food and make curry, which she was good at making, and became capable of preparing meal alone again, including aftercare of fire associated with the cooking. The patient was partially capable of participating social activities out of the home, which was previously difficult. At 5 months after starting the administration, symptoms were stable and the progression of cerebral atrophy was not observed in head imaging. Scores of MMSE increased to 17 or more. Since no reasons other than the administration of iguratimod were found for the suppression of progressive cerebral atrophy and the amelioration of the symptoms as described above, the administration of iguratimod is considered to be the causes thereof.

This example is a typical case of AZD not associated with CAA as judged by brain imaging. The administration of iguratimod suppressed progressive cerebral atrophy and ameliorated symptoms therewith, as observed in the case of Alzheimer-type dementia associated with CAA illustrated in Example 1.

As used herein, the statement "cerebral amyloid β storage diseases" is not a name of a single disease, but a group of diseases caused by abnormal accumulation of amyloid β (a degradation product of the amyloid β precursor protein (APP)) in the brain, which include AZD, which is caused by cognitive impairment, and multiple micro-bleeding, which is caused by the accumulation on the cerebrovascular wall, and CAA, which exhibits multiple, relapsing, and sometimes bilateral subcortical bleeding.

Recently, it has been revealed that nearly 90% of AZD patients have amyloid 1 accumulation on the cerebrovascular wall and patients with no amyloid β accumulation on the cerebrovascular wall did not develop AZD. It has been therefore considered that the accumulation of amyloid β on the vascular wall should be the cause of AZD development, recently (Non Patent Document 5). The cause of the accumulation of amyloid β on the vascular wall is considered to be disturbance in "excretion mechanism of amyloid β into the blood in the vessel (out of the brain)" mediated by macrophages migrating in the vascular wall. Furthermore, the cause thereof is supposed to be some kind of inflammatory responses occurring in the vascular wall. Examples (1) and (2) described above indicate that the inflammation that cannot be sufficiently suppressed with a steroid agent having a wide spectrum anti-inflammatory effect, that is, "the inflammatory response that is suppressed or blocked only by a specific effect of iguratimod and its analogs" causes the accumulation of amyloid β.

The invention claimed is:

1. A method for treating a cerebral amyloid β storage disease, comprising:
   administering to a patient in need thereof a compound represented by Formula (A) or a salt thereof,

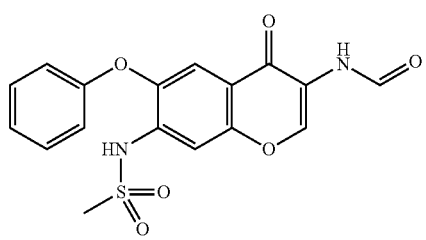

Formula (A)

wherein the cerebral amyloid β storage disease is Alzheimer-type dementia or cerebral amyloid angiopathy.

2. The method of claim 1, wherein the cerebral amyloid β storage disease is Alzheimer-type dementia.

3. The method of claim 1, wherein the cerebral amyloid β storage disease is cerebral amyloid angiopathy.

4. The method of claim 1, wherein the patient is suffering from at least one symptom selected from the group consisting of progression of dementia, central gait impairment, equilibration disorder, motor impairment, higher brain dysfunction, apraxia, agnosia, aphasia, incontinence, gait disturbance, anarthria, dysphagia, apathy and listlessness.

5. A method for suppressing a progression of cerebral atrophy caused by Alzheimer-type dementia, comprising:
   administering to a patient having Alzheimer-type dementia a compound represented by Formula (A) or a salt thereof,

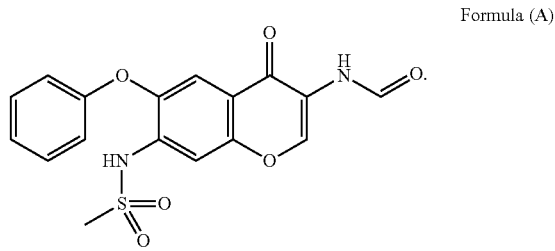 [SMILES: CS(=O)(=O)Nc1cc2occ(NC=O)c(=O)c2cc1Oc1ccccc1]

Formula (A)

6. A method for ameliorating a cognitive impairment caused by Alzheimer-type dementia, comprising:
   administering to a patient having Alzheimer-type dementia a compound represented by Formula (A) or a salt thereof,

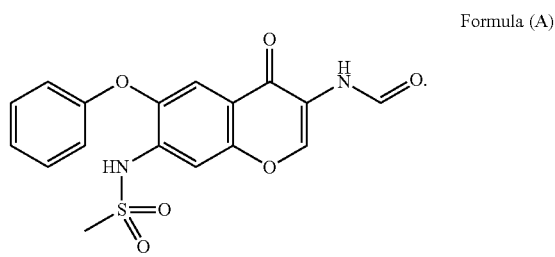 [SMILES: CS(=O)(=O)Nc1cc2occ(NC=O)c(=O)c2cc1Oc1ccccc1]

Formula (A)

7. A method for suppressing an increase or enlargement of intracerebral micro-bleeding caused by cerebral amyloid angiopathy, comprising:
   administering to a patient having a cerebral amyloid angiopathy a compound represented by Formula (A) or a salt thereof,

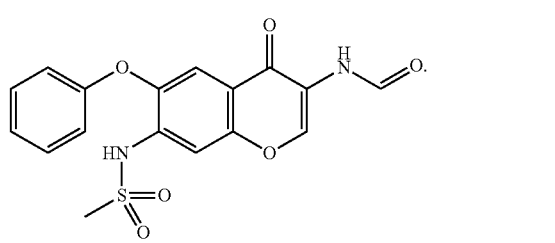

Formula (A)

* * * * *